United States Patent

Foote et al.

[11] Patent Number: 6,043,047
[45] Date of Patent: Mar. 28, 2000

[54] SAMPLE-COLLECTING AND ASSAY DEVICE FOR USE IN THE DETECTION OF BIOLOGICAL MATERIAL

[75] Inventors: Nicholas Peter Martin Foote; Peter Leonard Grant; Anthony Cooke; Ramin Pirzad, all of Cambridge, United Kingdom

[73] Assignee: Celsis International, PLC, United Kingdom

[21] Appl. No.: 09/012,281

[22] Filed: Jan. 23, 1998

Related U.S. Application Data

[63] Continuation-in-part of application No. 08/553,477, filed as application No. PCT/GB94/00783, Apr. 14, 1994, abandoned.

[30] Foreign Application Priority Data

Apr. 23, 1993 [GB] United Kingdom ............ 9308411

[51] Int. Cl.⁷ ............... C12Q 1/42; C12Q 1/54; C12Q 1/48; C12Q 1/26
[52] U.S. Cl. ............... 435/21; 435/14; 435/15; 435/26; 435/28; 435/25
[58] Field of Search ............... 435/21, 14, 15, 435/25, 26, 28

[56] References Cited

U.S. PATENT DOCUMENTS

| | | | |
|---|---|---|---|
| 3,745,090 | 7/1973 | Chappelle et al. | 435/15 |
| 4,234,313 | 11/1980 | Faulkner | 435/15 |
| 4,277,562 | 7/1981 | Modrovich | 435/15 |
| 4,303,752 | 12/1981 | Kolehmainen et al. | 435/15 |
| 4,371,624 | 2/1983 | Saxholm | 435/15 |
| 4,493,815 | 1/1985 | Fernwood et al. | 435/15 |
| 4,495,293 | 1/1985 | Shaffar | 435/15 |
| 4,584,272 | 4/1986 | Imahori et al. | 435/15 |
| 4,735,897 | 4/1988 | Vary et al. | 435/15 |
| 4,767,699 | 8/1988 | Vary et al. | 435/15 |
| 4,923,796 | 5/1990 | Deneke et al. | 435/15 |
| 5,001,055 | 3/1991 | Imahori et al. | 435/15 |

FOREIGN PATENT DOCUMENTS

| | | |
|---|---|---|
| 0060123 | 9/1982 | European Pat. Off. . |
| 0102504 | 3/1984 | European Pat. Off. . |
| 0193895 | 9/1986 | European Pat. Off. . |
| 0327952 | 8/1989 | European Pat. Off. . |
| 1-023900 | 1/1989 | Japan . |
| 2055200 | 2/1981 | United Kingdom . |

OTHER PUBLICATIONS

Chittock et al. (1991) "Light Amplification by a Coupled Biological System: ATP, Firefly Luciferase and Recycling of ATP". Biochemical Society Transactions. 19(160S).

*Primary Examiner*—Louise N. Leary
*Attorney, Agent, or Firm*—Saliwanchik, Lloyd & Saliwanchik

[57] ABSTRACT

An assay device comprises a tube, a removable top part and a bottom part, wherein an elongate member with a swab at its distal end is mounted on the top part, the top part includes a compartment containing liquid and partly defined by a first frangible membrane that can be ruptured to release the liquid into the tube, and the bottom part contains a reagent and is partly defined by a second frangible membrane that can be ruptured on movement of the bottom part relative to the tube.

Reaction occurring in the bottom part can be observed through a window. This reaction may be of the type involving amplification of say, ATP, e.g. by providing AMP, glucose-6-phosphate (G6P), adenylate kinase, glucokinase and reagents that convert glucose (G) to give a color, whereby the following reactions occur $$AMP + ATP \rightarrow 2ADP$$

$$G6P + ADP \rightarrow ATP + G.$$

7 Claims, 9 Drawing Sheets

FIG. 8

SAMPLE-COLLECTING AND ASSAY DEVICE FOR USE IN THE DETECTION OF BIOLOGICAL MATERIAL

CROSS-REFERENCE TO A RELATED APPLICATION

This application is a continuation-in-part of U.S. Ser. No 08/553,477, filed Oct. 20, 1995, now abandoned, which is a U.S. national stage application filed from International patent application No. PCT/GB94/00783, filed Apr. 14, 1994.

FIELD OF THE INVENTION

This invention relates to a sample-collecting and assay device, and in particular to a simple hygiene monitor. The device may be used in the detection of biological material, e.g. utilizing a novel reaction mechanism also defined herein.

BACKGROUND OF THE INVENTION

Many techniques are available for the detection of biological materials, for instance by the production of a colour. For example, materials may be added that form hydrogen peroxide or NADH in the presence of the target substance, and these may be caused to produce a coloured compound by further reactions. Alternatively, the target substance may produce colour more directly; for instance, many hydrolytic enzymes can act on artificial substrates to give a coloured product.

A difficulty arises, however, in connection with the detection of very small amounts of the target substance, such that the amount of colour produced may be too small to analyse without complicated apparatus, and certainly not by the naked eye. Some amplification mechanisms have been described, such as cyclic reactions for the measurement of low levels of NAD(H) or NADP(H); see EP-A-0060123. This is an example of a cycle giving linear amplification of the target substances, i.e. their concentrations increase in proportion with reaction time, and therefore a long period is required for sensitive measurements.

GB-A-2055200 discloses the same and other linear amplification cycles. It also discloses a cycle wherein adenylate kinase catalyzes the reaction of AMP and ATP to form ADP which is then re-phosphorylated to form ATP by the action of pyruvate kinase. It is stated that, in each cycle, one extra molecule of ATP is produced. The reaction is used to amplify ATP for the purposes of bioluminescence. The procedure for ATP amplification involves adding the other materials sufficient for the reactions to proceed, stopping the cycling reaction, and measuring accumulated ATP using a bioluminescence assay and a luminometer.

Chittock et al. Biochemical Society Transactions (1991) 19:160S, also disclose that the light intensity of the known bioluminescence reaction may be increased by recycling ATP in a system containing myokinase (adenylate kinase), pyruvate kinase, phosphoenolpyruvate and AMP. The authors consider the fate of two molecules of ATP present initially in the sample. One molecule is consumed by the luciferase reaction and is converted to AMP. It can then undergo a reaction with the other molecule of ATP, in a reaction catalyzed by myokinase (adenylate kinase), to form two molecules of ADP. These are subsequently re-phosphorylated by reaction with phosphoenolpyruvate, catalysed by pyruvate kinase, to regenerate the original two molecules of ATP. The added AMP is described as a "trap" for ATP which helps to get the recycling reaction underway.

It is not clear from the reaction scheme proposed by Chittock et al why the proposed ATP recycling mechanism should cause the observed increase in peak light output of the luciferase reaction, since no net increase in ATP concentration would occur. Nevertheless, the authors describe the phenomenon as amplification of ATP.

WO-A-9525948 discloses a sample-collecting and assay device comprising a tube, a removable top part and a bottom part, wherein an elongate member with a swab at its distal end is mounted on the top part. There may be one or more foil-sealed bottom parts fixed within the tube, and the foils are successively broken by movement of the swab, or a coaxially-extending blade-like member, through the tube.

WO-A-9703209 discloses a similar device, in which reagent is contained in a bottom part with a window, and which has a seal broken by movement of the swab through the tube. Another, similar device is disclosed in WO-A-9723596.

SUMMARY OF THE INVENTION

An assay device according to the present invention is for use in determining the presence in a liquid sample of a target component that, in combination with other components, undergoes a reaction to give a detectable signal. The novel device comprises a tube, a removable top part and a bottom part, wherein an elongate member with a swab at its distal end is mounted on the top part, the top part includes a compartment containing liquid and partly defined by a first frangible membrane that can be ruptured to release the liquid into the tube, and the bottom part contains a reagent and is partly defined by a second frangible membrane that can be ruptured on movement of the bottom part relative to the tube.

By means of the invention, direct analysis can be made, by observing the signal generated, in the bottom part. Although the novel device shares many characteristics with the prior art devices, described above, its particular advantages include the use of a simple visual test with a yes/no result, avoiding the need for a luminometer, and a syringe-like mechanism within the top dispenser, to ensure repeatable and reproducible dispensing of liquid reagent. The test can have high sensitivity. Although the top part may be unitary or comprise a separate component containing reagent, the design of the top reagent container and its holder may be such that a single operation, depressing the container, ruptures the seal and evacuates the contents of the container down the swab shaft, ensuring accurate and reproducible dispensing of the liquid reagent with minimal dead volume and without introduction of any air, unlike a "pumping" dispensing system.

Further, it has now been appreciated that there is a reaction system that can be used, not simply for the regeneration of ATP, but for the production of a colour or other easily-detectable signal which can be used to quantify very low levels of ATP and ADP. The signal may be visible, avoiding the previous requirement for additional apparatus such as a luminometer.

Figure 1:
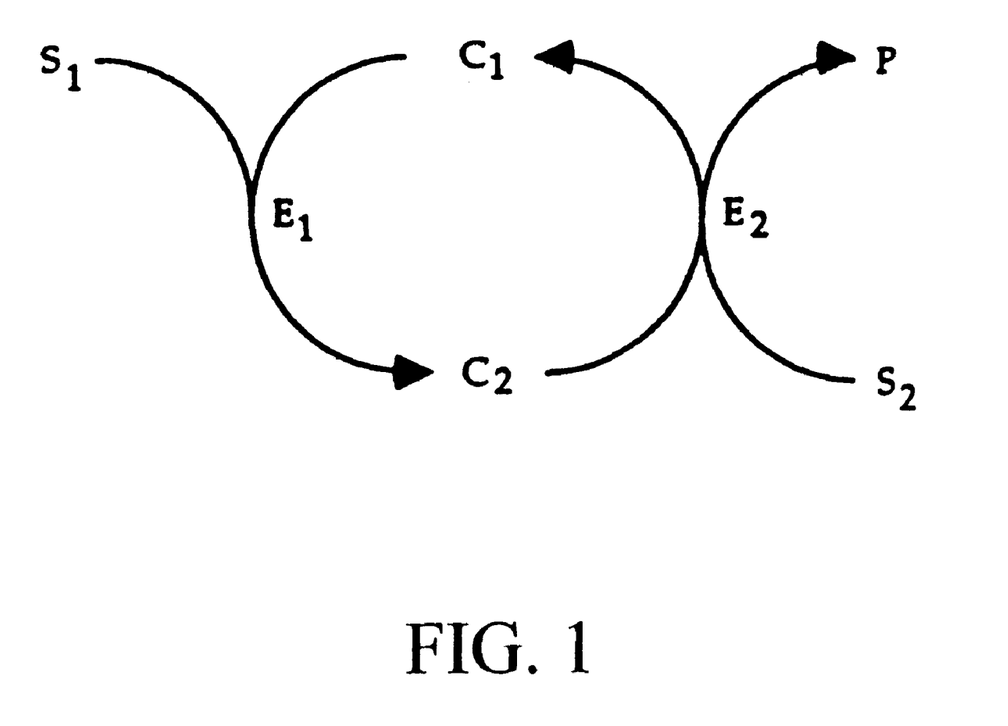
FIGS. 1 to 5 are each schemes of reactions, more or less general, that may be utilised in the present invention.

More generally, according to the present invention, coupled reactions of the type shown below in FIG. 1 are used to detect the presence of either or both of the interconvertible compounds $C_1$ and $C_2$ or of the enzymes $E_1$ and $E_2$, by the provision of the other components of the cycle necessary for the reactions to proceed, including the respective enzyme substrates $S_1$ and $S_2$, and observation of the loss of a substrate ($S_1$ or $S_2$) or, preferably, the formation of a product (P). By comparison with the procedure disclosed in GB-A-

2055200, the exponential amplification is used for the observation of an extra-cyclic component.

Observation may be direct or by coupling the reactions to a system that gives a detectable derivative (or derivative reaction) and which may be known per se. Advantages associated with the present invention are that a yes/no result can be obtained, that the reaction is quick, and that it can be used to detect microorganisms.

BRIEF DESCRIPTION OF THE DRAWINGS

Abbreviations used in FIGS. 4 and 5, and elsewhere, have the following meanings:
AMP: Adenosine 5'-monophosphate
ADP: Adenosine 5'-diphosphate
ATP: Adenoise 5'-triphosphate
G6P: D-Glucose 6-phosphate
G: D-Glucose
AAP: 4-Aminoantipyrine
DMA: N,N-dimethylaniline
$G_{OX}$: D-Glucono-1,5-lactone
AK: Adenylate kinase
GK: Glucokinase
GO: Glucose oxidase
HRP: Horseradish peroxidase
G1P: D-Glucose 1-phosphate
G1,6DP: D-Glucose 1,6-biphosphate
3PGP: 3-Phospho-D-glyceroyl phosphate
3PG: 3-Phospho-D-glycerate
3PHP: 3-Phosphohydroxypyruvate
GPPDM: Glucose-1-phosphate phosphodismutase
GBPS: Glucose-1,6-biphosphate synthase
PGDH: Phosphoglycerate dehydrogenase
DPA: Diaphorase
Col: Color
INV: INT-violet
Fzn: Formazan.

DESCRIPTION OF THE INVENTION

The coupled reactions on which the present invention is based are illustrated generally by FIG. 1. By way of illustration only, a description of how the cycle can be used to detect a pair of interconvertible compounds $C_1$ and $C_2$ is given below. A similar mechanism would apply for the detection of one or both of the enzymes $E_1$ and $E_2$.

The reaction catalyzed by enzyme $E_1$ is a "comproportionation" reaction, in which one molecule of the first target compound $C_1$ reacts with one molecule of added substrate $S_1$ to form two molecules of the second target compound $C_2$. By the action of enzyme $E_2$ and its co-substrate $S_2$, these two molecules of $C_2$ are now converted to two molecules of the first target compound $C_1$ which are available as substrates for the enzyme $E_1$. Thus one molecule of the first target compound has been converted to two: another turn of the cycle will produce four, yet another eight, etc.

More specifically, the reactions that take place in cycles 1, 2 and 3 are as follows:

1) $C_1+S_1 \rightarrow 2C_2$ and $2C_2+2S_2 \rightarrow 2C_1+2P$
2) $2C_1+2S_1 \rightarrow 4C_2$ and $4C_2+4S_2 \rightarrow 4C_1+4P$
3) $4C_1+4S_1 \rightarrow 8C_2$ and $8C_2+8S_2 \rightarrow 8C_1+8P$ In this way, an exponential amplification of a target compound occurs. Molecules of the second target compound present initially will be amplified in a similar way.

With reference to FIG. 1, there is a choice of methods by which the progress of the cycle may be followed. As the cycle proceeds, the concentrations of $S_1$ and $S_2$ will decrease, whilst the concentrations of $C_1$, $C_2$ and P will increase. Any of these changes in concentration of an extra-cyclic material might be suitable for linking to, by way of example, the production or loss of a colored compound. If it is not possible to cause a color change to occur in the same reaction system as the amplification cycle, then samples could be removed for separate analysis; removal of P may facilitate the cyclic reactions.

Figure 2:
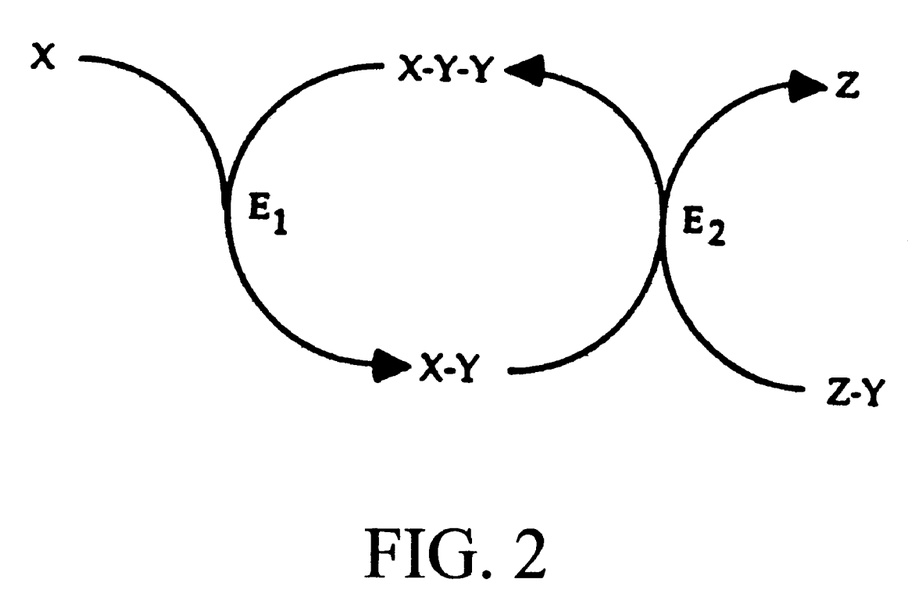
Figure 3:
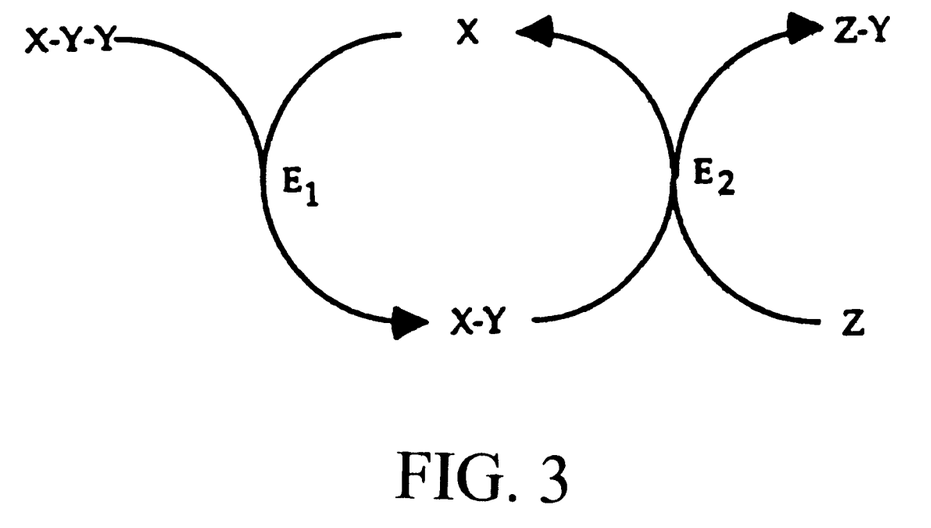

FIGS. 2 and 3 illustrate more specific examples of the invention, in which interconversion of the two target compounds involves transfer of a chemical group. More generally, analogous mechanisms exist involving, for instance, transfer of one or more electrons between redox-active substances.

X-Y-Y and X-Y in FIG. 2 might be compounds such as ATP and ADP respectively, which differ only by one phosphate group. Enzyme $E_1$ in this case would be adenylate kinase (E.C.2.7.4.3) which catalyses the "comproportionation" reaction in which one molecule of the first target substance X-Y-Y (e.g. ATP) reacts with one molecule of added substrate X(e.g. AMP) to form two molecules of the second target substance X-Y(e.g. ADP). Enzyme $E_2$ in this example could be a kinase which, together with added phosphorylated co-substrate Z-Y, would phosphorylate ADP to ATP.

FIG. 3 shows an alternative cycle in which the flow of the chemical group Y is, essentially, in the opposite direction. In this case, the two target compounds are X and X-Y.

Figure 4:
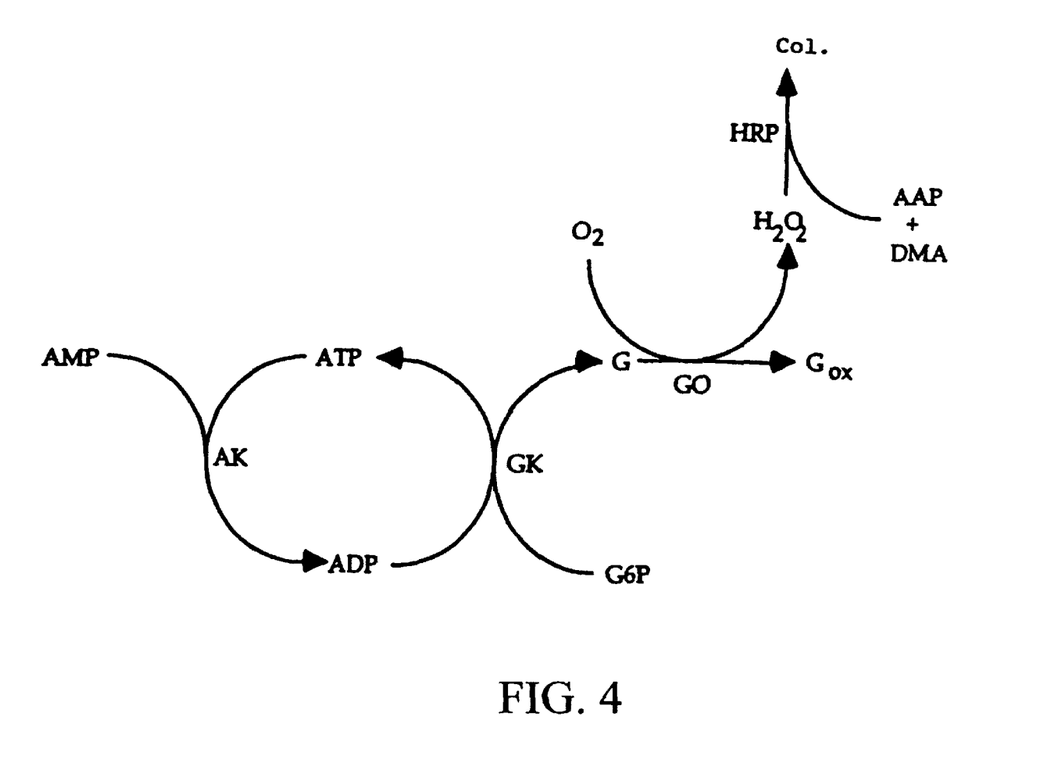

FIG. 4 illustrates the linking of the enzymatic cycle of FIG. 2 to color production, for the case of ADP/ATP amplification. Enzyme $E_1$ is adenylate kinase and enzyme $E_2$ is glucokinase, which produced D-glucose and ATP from D-glucose-6-phosphate and ADP. The increase in concentration of glucose is shown to be monitored by the linked reactions of glucose oxidase (E.C. 1.1.3.4) and horseradish peroxidase (E.C. 1.11.1.7) together with suitable chromogenic substrates. Many alternative kinase enzymes to serve as $E_2$ are available together with their specific co-substrate: for instance, pyruvate kinase (E.C. 2.7.1.40) with phosphoenolpyruvate, acetate kinase (E.C. 2.7.2.1) with acetyl phosphate. NADH kinase (E.C. 2.7.1.86) with NADPH, fructokinase (E.C. 2.7.1.4) with D-fructose-6-phosphate, or glycerol kinase (E.C. 2.7.1.30) with glycerol-3-phosphate. In fact, many enzymes from the group 2.7 in the IUB Recommendations on Enzyme Nomenclature (1984, Academic Press) might be used in such a scheme. In each case, the product may be detected by a specific enzyme reaction, a series of enzyme reactions, or a chemical reaction, producing or destroying a color.

If desired, contaminating levels of ATP and ADP in the amplifying reagent can be lowered by an initial incubation of the components of the reagent with an enzyme such as potato apyrase (E.C. 3.6.1.5) which hydrolyses both ATP and ADP to AMP. Provided it is at a low concentration, the presence of apyrase will not interfere with the amplification cycle.

Thus a reagent for the detection of ATP and/or ADP might comprise AMP, adenylate kinase, glucokinase, D-glucose- 6-phosphate, glucose oxidase, apyrase, horseradish peroxidase and one or more chromogenic peroxidase substrates in a suitable buffer system containing magnesium ions. Since the cycle is essentially exponential, a low amount of ADP or ATP (perhaps a single molecule) present in the complete reagent will rapidly be multiplied until one of the substrates is exhausted. If desired, the reagent may be prepared as two or more separate solutions which are mixed together at approximately the same time as a sample for assay is added.

FIGS. 2 and 4 show that one of the interconvertible compounds which can be detected is ATP. The present invention is thus particularly suitable as a ready test for the presence of microorganisms. A liquid sample containing a very low concentration of microorganisms can be tested by, for example, presentation on a carrier, e.g. a multi-well plate, and adding the necessary reagents for the reaction to proceed. The process described in WO-A-9319199 may be used to retain microorganisms in wells, even when at very low concentration in a liquid sample. The present invention can detect the microorganisms in each well, giving a result that is available to the naked eye, within a reasonable period of time.

Figure 5:
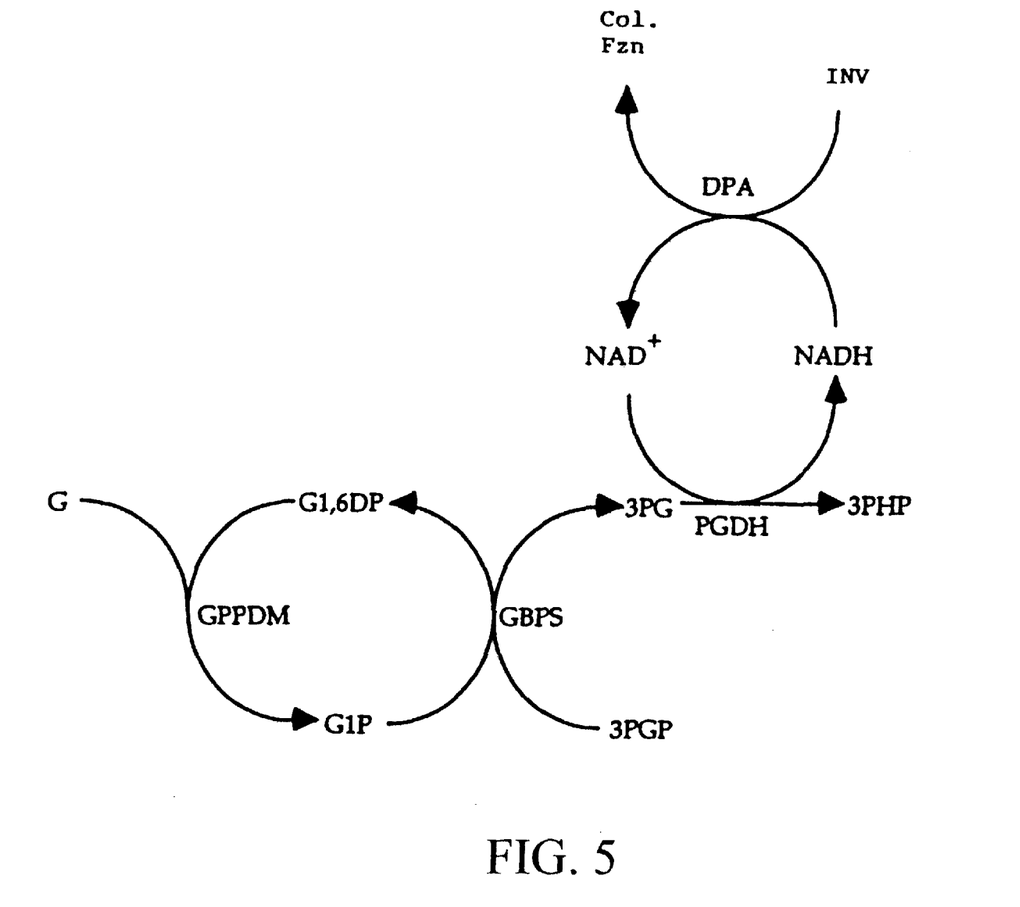

Alternatives to the ATP/ADP amplification cycle exist. The requirements are (i) an enzyme catalysing a comproportionation reaction, such that the presence of one molecule of the first target substance causes the formation of two molecules of the second target substance, and (ii) an enzyme which catalyses the formation of the first target substance from the second. An example is shown in FIG. 5. Here, $E_1$ is glucose-1-phosphate phosphodismutase (E.C. 2.7.1.41), $E_2$ is glucose-1,6-biphosphate synthase (E.C. 2.7.1.106), and the target substances are D-glucose-1,6-bisphosphate and D-glucose-1-phosphate. Progress of the amplification cycle may be followed by using the 3-phospho-D-glycerate produced by $E_2$ as a substrate for the enzyme phosphoglycerate dehydrogenase (E.C. 1.1.1.95), producing NADH which can be used to form a color by chemical or enzymatic means: for instance, the reaction with INT-violet catalysed by the enzyme diaphorase (E.C. 1.8.1.4).

A device of this invention is particularly suitable for determining the presence of organic matter, including food residues, and microorganisms, in which case the target component may be ATP. This aspect of the invention will now be described by way of example only with reference to this embodiment.

Further, again for the purpose of illustration, the invention will be described with reference to reactions of the type described, i.e. involving enzymes and their substrates. These materials constitute the components that, in combination, undergo the reaction that gives the detectable signal. Such a reaction includes the following:

wherein G is glucose and G6P is glucose-6-phosphate. These reactions are catalysed by adenylate kinase and glucokinase. Glucose is then converted to give a colour, in a further enzymatic sequence, e.g. utilizing glucose oxidase (GO) and horseradish peroxidase (HRP). Although, glucose or $H_2O_2$ may be detected by, say, electrochemical means.

Alternatively, in use of the novel device, the analyte may be detected by bioluminescence. Suitable reagents etc. are described in WO-A-9525428, the content of which is incorporated herein by reference.

The reaction components may be present together in the bottom part, in a freeze-dried mixture.

In use of a device of the invention, a sample, e.g. of microorganisms obtained by swabbing, is provided and the reagents and liquid are mixed with them. Especially if the reaction generates a color, comparison of that and a standard can be made readily, to give a quick indication of the concentration of the analyte in the sample.

Figure 7A:
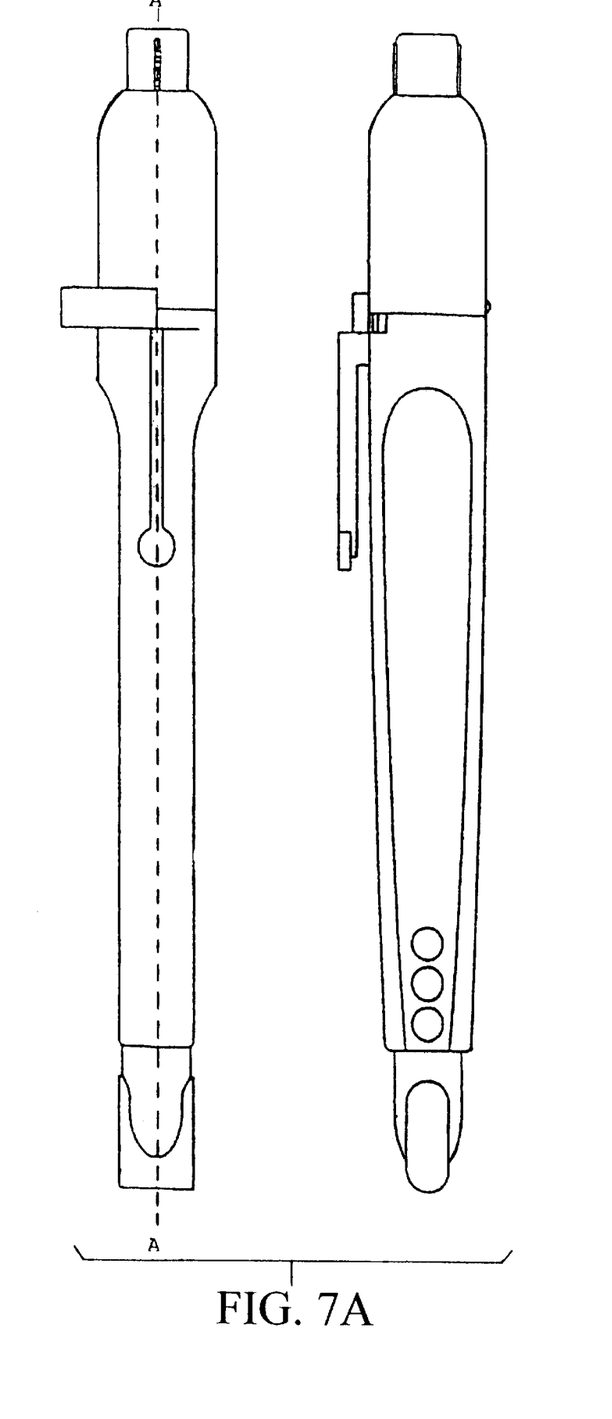
FIG. 7A shows separate side views of a device embodying the invention.
Figure 7B:
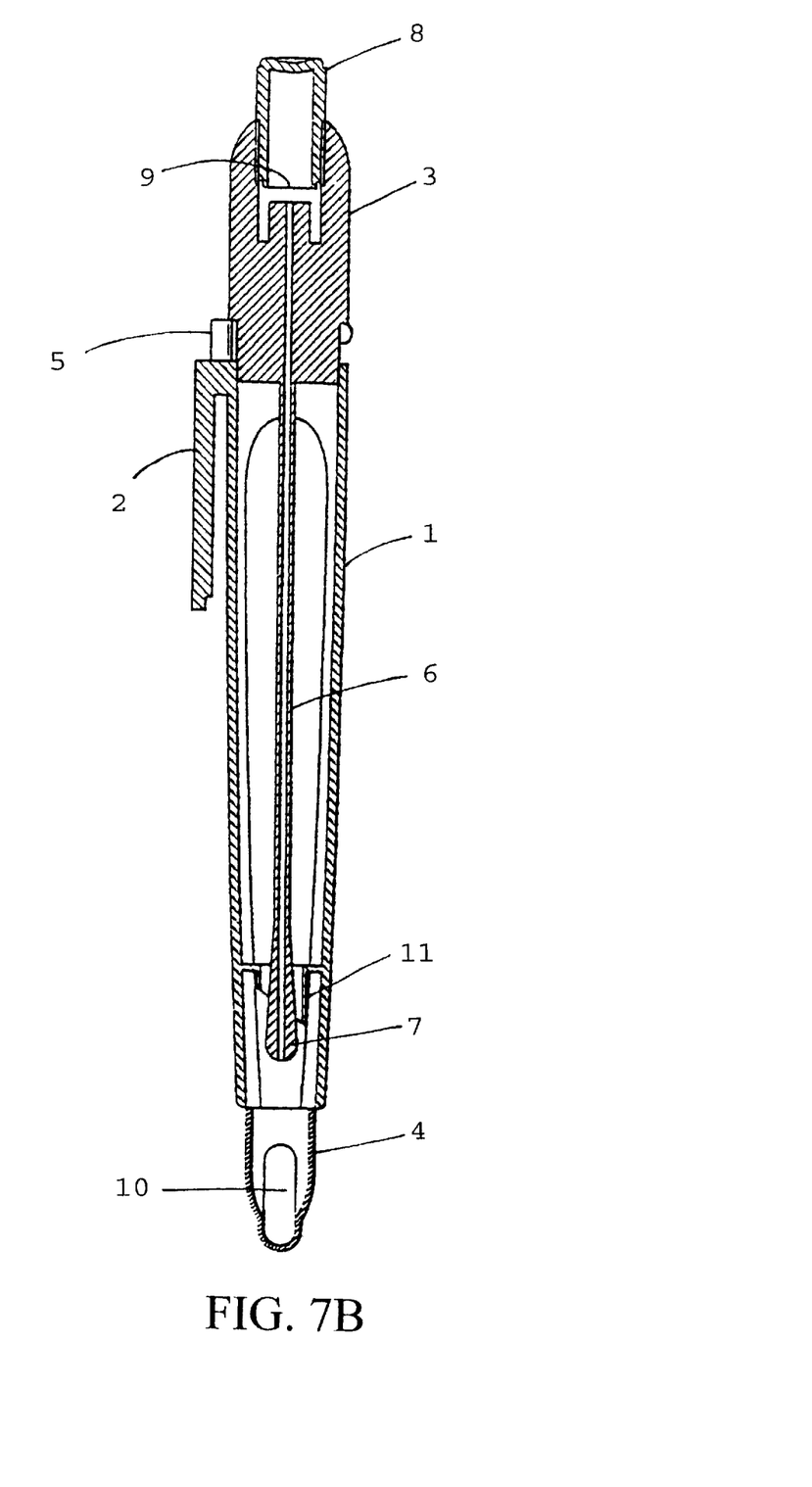
FIG. 7B is a cross-section of the same embodiment, along the line A—A in FIG. 7A.
Figure 8:
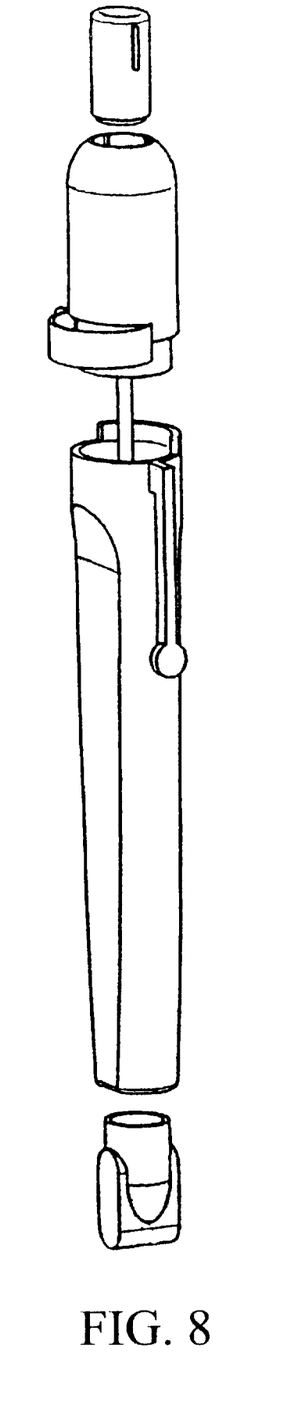
FIG. 8 is an exploded view of the embodiment shown in FIG. 7.

For simplicity, a device of the invention will be described with reference to FIG. 7B. The embodiment illustrate there comprises a tube 1 with a pen-type holder 2. A top part 3 and a bottom part 4 are each mounted on the tube and each can be pushed into close engagement with the tube. In the case of the top part, close engagement is prevented, until required, by the removable or peelable safety seal 5.

The top part 3 has mounted thereon a tubular elongate member 6 that terminates in a swab 7. The top part 3 also comprises a separate component 8 which is a compartment having a foil seal 9. On depression of this component, the foil seal is ruptured, and a known amount of liquid is discharged down the elongate member to the swab 7, within the tube 1.

The bottom part 4 is in the form of a foil-sealed cuvette including a window 10. It may contain freeze-dried reagent (s). The foil is broken by pushing the part 4 inwardly with respect to the tube 1. The foil may be broken on the swab or on an angled blade-like member 11 provided as an internal component of the tube 1.

In use, the top part 3 is removed from the tube 1, a sample is taken up on the swab 7, and this is replaced in the tube. The seal on the bottom part 4 is then broken. The safety seal 5 is then removed, and the component 8 pushed inwards, to release a known quantity of liquid. Results can be read through the window 10. A qualitative assessment can be made by comparison of the color generated with reference spots of different color intensity (of which three are shown in FIG. 7A).

The following Examples illustrate the invention.

EXAMPLE 1

Two reagent pre-mixes, A and B, were prepared with the following compositions (MES=2-(N-morpholino)ethane-sulphonic acid):

| Pre-mix A | |
|---|---|
| D-glucose 6-phosphate | 2.67 mM |
| Adenosine 5'-monophosphate (AMP) | 1.33 mM |
| Adenylate kinase | 0.27 U/ml |
| Bovine serum albumin | 0.2 mg/ml |
| EDTA | 0.67 mM |
| 4-Aminoantipyrine | 1.33 mM |
| N,N-dimethylaniline | 3.33 mM |
| Magnesium chloride | 20 mM |
| Potassium chloride | 40 mM |
| Potato apyrase | 0.04 U/ml |
| MES pH 6.0 | 100 mM |
| Pre-mix B | |
| Glucose oxidase | 320 U/ml |
| Glucokinase | 80 U/ml |
| Horseradish peroxidase | 32 U/ml |
| Bovine serum albumin | 0.2 mg/ml |
| Magnesium chloride | 20 mM |
| Potassium chloride | 40 mM |
| Potato apyrase | 0.04 U/ml |
| MES pH 6.0 | 100 mM |

The premixes were incubated separately at 25° C. for 3 hours, to destroy contaminating ATP and ADP. Then, in each of three cuvettes, 0.225 ml of Pre-mix A was mixed with 0.075 ml of Pre-mix B, and 0.3 ml of a sample was immediately added. The samples comprised water (as a blank), 20 pM ATP and 200 pM ATP. The absorbance at 555 nm in each cuvette was followed in a spectrophotometer during incubation for 200 minutes at 25° C.

Figure 6:
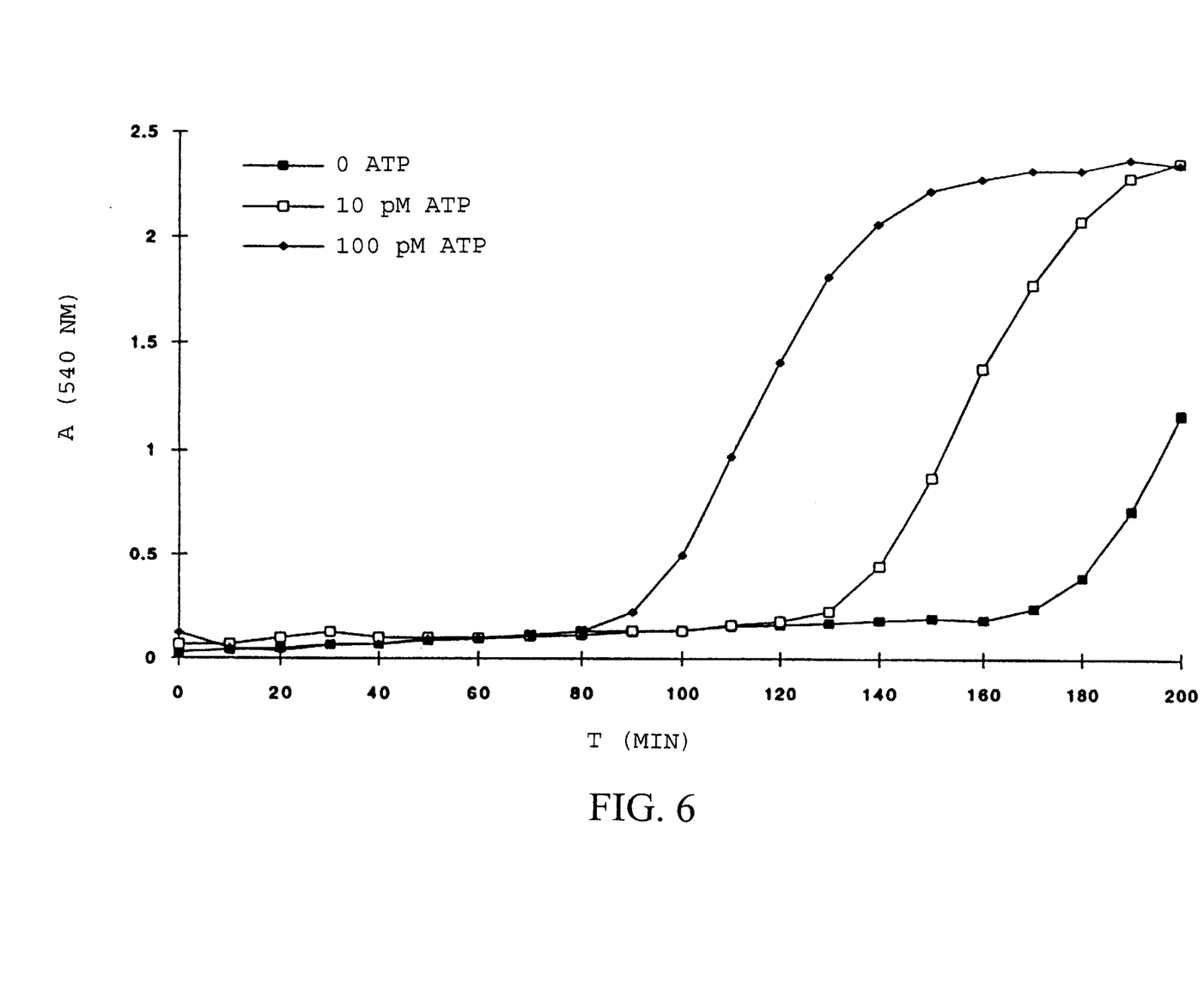
FIG. 6 is a graph representing results obtained by use of the invention.

Plots of absorbance (A) with respect to time (T) are presented in FIG. 6. It should be noted that, after a reaction time of approximately 150 minutes, the three samples could easily be distinguished by eye. The more ATP that was added, the sooner a violet color appeared in the solution.

EXAMPLE 2

A similar reagent composition was used for the rapid enumeration of *E. coli* using the most probable number technique. This approach is based on dilution of the culture and its even distribution into a number of compartments (in this case 24 per sample), with dilutions chosen such that each set is likely to include compartments with either no bacteria or a small number. Addition of growth medium then allows multiplication of the bacteria to levels that can be detected, and the number of compartments positive for growth gives an estimate of the sample bacterial population. This general technique is described in WO-A-9319199.

A microtitre plate with 0.2 μm membrane at the bottom of each well was set up as follows, using dilutions of an overnight culture of *E. coli* in 0.9% (w/v) NaCl containing 5 mM magnesium chloride:
Columns 1–6: 0.04 ml diluent
Columns 7–9: 0.004 ml *E. coli*, $10^{-2}$ dilution
Columns 10–12: 0.004 ml *E. coli*, $2.5 \times 10^{-2}$ dilution.

Vacuum was applied to removed the liquid and to collect the bacteria on the membrane filters. 0.1 ml of sterile yeast extract-peptone broth was then added to each well, and the microplate was covered and incubated at 37° C. for 8.5 hours.

At the end of the incubation period, the broth was removed by vacuum, and the wells were each washed with 0.25 ml of sterile diluent in order to remove non-microbial ADP and ATP (which are present in broth). After vacuuming again, 0.025 ml of 0.22% (w/v) chlorohexidine digluconate (a cationic detergent used for lysing bacteria) was added to each well, followed by 0.025 ml of diluent. For columns I-6, the diluent was spiked with various concentrations of ATP between 0 and $6 \times 10^{-9}$ M.

The two Pre-mixes, similar to Example 1 but with concentrations of the constituents adjusted to take account of the different sample volume in this experiment, were rapidly mixed together and 0.1 ml volumes were immediately added to each well. The plate was placed in a CERES 900 HDi microplate reader (Bio-Tek) incubated at 30° C., and the absorbances were measured at 550 nm for up to three hours.

Clear results were obtained after 70 minutes. At this point, in columns I-6, only the highest ATP standard ($10^{-9}$ M in the final reaction mixture) had developed a measurable amount of color. In columns 7–12, the absorbance in the wells was either very close to the starting value (i.e. a negative) or was clearly detectable (a positive, showing that at least one bacterium had been present initially). Columns 7–9 had 15 positives, which equates to a most probable number of 24.5 per ml (95% confidence range 13–42), and columns 10–12 had 21 positives, giving a most probable number of 52 per ml (95% confidence range 28–91). conventional plate counts on yeast extract-peptone agar of the initial *E. coli* culture gave estimates of 29 and 71 cfu/ml respectively for the two dilutions.

The procedure therefore took less than 10 hours to enumerate the *E. coli* samples. The degree of colour development was sufficient to allow reading of the plate by eye.

What is claimed is:

1. A method for detecting in a sample or host the presence of any of the materials X-Y, X-Y-Y, enzyme $e_1$ and enzyme $e_2$ that undergo the following reactions $$X + X\text{-}Y\text{-}Y \xrightarrow{e_1} 2X\text{-}Y$$
$$X\text{-}Y + Z\text{-}Y \xrightarrow{e_2} X\text{-}Y\text{-}Y + Z$$

which comprises adding the other materials sufficient for the reactions to proceed, and observing the loss of X or Z-Y or the formation of Z, wherein X and Z are biological compounds capable of covalently binding a phosphate group, $e_1$ is a phosphatase, $e_2$ is a phosphate transferase, and Y is a phosphate group.

2. The method according to claim 1, wherein Z-Y is phosphoenolpyruvate or glucose-6-phosphate.

3. The method according to claim 1, wherein X, X-Y and X-Y-Y are nucleotide phosphates.

4. The method according to claim 3, wherein X, X-Y and X-Y-Y are AMP, ADP and ATP, respectively.

5. The method according to claim 4, for detecting ADP and/or ATP.

6. The method according to claim 5, for detecting microorganisms.

7. A method for detecting the presence of microorganisms containing ATP, or ADP, in a sample, which comprises providing AMP, glucose-6-phosphate (G6P), adenylate kinase, glucokinase and reagents that convert glucose (G) to give a color, whereby the following reactions occur $$AMP + ATP \rightarrow 2ADP$$

$$G6P + ADP \rightarrow ATP + G.$$

* * * * *

UNITED STATES PATENT AND TRADEMARK OFFICE
CERTIFICATE OF CORRECTION

PATENT NO. : 6,043,047  
DATED : March 28, 2000  
INVENTOR(S) : Nicholas Peter Martin Foote, Peter Leonard Grant, Anthony Cooke, Ramin Pirzard

Page 1 of 1

It is certified that error appears in the above-identified patent and that said Letters Patent is hereby corrected as shown below:

<u>Column 8,</u>  
Line 22, "2X-Y" should read -- 2 X-Y --.

Signed and Sealed this

Twenty-sixth Day of March, 2002

*Attest:*

*Attesting Officer*

JAMES E. ROGAN  
*Director of the United States Patent and Trademark Office*